US012773230B2

(12) United States Patent
Vo et al.

(10) Patent No.: US 12,773,230 B2
(45) Date of Patent: Oct. 27, 2026

(54) SHOCK WAVE CATHETER WITH DIFFERENTLY SIZED SHOCK WAVE EMITTERS

(71) Applicant: Shockwave Medical, Inc., Santa Clara, CA (US)

(72) Inventors: Khanh Vo, Daly City, CA (US); Tommy Nguyen, Santa Clara, CA (US); Raymond Chester Estrada, Dublin, CA (US); Huy Phan, Santa Clara, CA (US); Denny Kat-Kuoy, Santa Clara, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 165 days.

(21) Appl. No.: 18/923,312

(22) Filed: Oct. 22, 2024

(65) Prior Publication Data

US 2025/0127530 A1 Apr. 24, 2025

Related U.S. Application Data

(60) Provisional application No. 63/592,502, filed on Oct. 23, 2023.

(51) Int. Cl.
*A61B 17/22* (2006.01)
*A61B 17/00* (2006.01)

(52) U.S. Cl.
CPC .. *A61B 17/22022* (2013.01); *A61B 17/00234* (2013.01); *A61B 2017/00017* (2013.01);
(Continued)

(58) Field of Classification Search
CPC ........ A61B 17/22022; A61B 17/00234; A61B 2017/00017; A61B 2017/00238;
(Continued)

(56) References Cited

U.S. PATENT DOCUMENTS

| | | | |
|---|---|---|---|
| 2,916,647 | A | 12/1959 | George |
| 3,412,288 | A | 11/1968 | Ostrander |

(Continued)

FOREIGN PATENT DOCUMENTS

| | | | |
|---|---|---|---|
| AU | 2009313507 | B2 | 11/2014 |
| AU | 2013284490 | B2 | 5/2018 |

(Continued)

OTHER PUBLICATIONS

Unpublished U.S. Appl. No. 18/586,299 (Rond et al.), filed Feb. 23, 2024, titled "Locus Emitter Shock Wave Catheter Devices With Increased Longevity and Higher Sonic Output," (Copy not submitted herewith pursuant to the waiver of 37 C.F.R. § 1.98(a)(2)(iii)).

(Continued)

*Primary Examiner* — Phong Son H Dang
(74) *Attorney, Agent, or Firm* — Morrison & Foerster LLP

(57) ABSTRACT

A catheter for treating a lesion in a body lumen includes an elongate member, an enclosure, and shock wave emitters enclosed by the enclosure. At least one of the shock wave emitters has a different size than at least one of the other emitters. Providing a smaller shock wave emitter at a distal end of the catheter can help make the catheter more navigable through the body lumen.

31 Claims, 8 Drawing Sheets

(52) U.S. Cl.
CPC ............... *A61B 2017/00238* (2013.01); *A61B 2017/00305* (2013.01); *A61B 2017/00477* (2013.01); *A61B 2017/00929* (2013.01); *A61B 2017/22025* (2013.01); *A61B 2017/22028* (2013.01); *A61B 2017/22064* (2013.01)

(58) Field of Classification Search
CPC ........... A61B 2017/00305; A61B 2017/00477; A61B 2017/00929; A61B 2017/22025; A61B 2017/22028; A61B 2017/22064
See application file for complete search history.

(56) References Cited

U.S. PATENT DOCUMENTS 3,413,976 A 12/1968 Roze
3,524,101 A 8/1970 Barbini
3,583,766 A 6/1971 Padberg
3,785,382 A 1/1974 Schmidt-Kloiber et al.
3,902,499 A 9/1975 Shene
3,942,531 A 3/1976 Hoff et al.
4,027,674 A 6/1977 Tessler et al.
4,030,505 A 6/1977 Tessler
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,878,495 A 11/1989 Grayzei
4,890,603 A 1/1990 Filler
4,900,303 A 2/1990 Lemelson
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,804 A 4/1992 Abele et al.
5,116,227 A 5/1992 Levy
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,454,809 A 10/1995 Janssen
5,472,406 A 12/1995 de la Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 de la Torre et al.
5,709,676 A 1/1998 Alt
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Dornhofer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,113,560 A 9/2000 Simnacher
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 de la Torre et al.
6,440,124 B1 8/2002 Esch et al.
6,494,890 B1 12/2002 Shturman et al.
6,514,203 B2 2/2003 Bukshpan
6,524,251 B2 2/2003 Rabiner et al.
6,589,253 B1 7/2003 Cornish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,939,320 B2 9/2005 Lennox
6,989,009 B2 1/2006 Lafontaine
7,066,904 B2 6/2006 Rosenthal et al.
7,087,061 B2 8/2006 Chernenko et al.
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton
7,951,111 B2 5/2011 Drasler et al.
8,162,859 B2 4/2012 Schultheiss et al.
8,177,801 B2 5/2012 Kallok et al.
8,353,923 B2 1/2013 Shturman
8,556,813 B2 10/2013 Cioanta et al.
8,574,247 B2 11/2013 Adams et al.
8,888,788 B2 11/2014 Hakala et al.
8,974,445 B2 * 3/2015 Warnking .............. A61N 7/022 601/3
9,044,618 B2 6/2015 Hawkins et al.
9,044,619 B2 6/2015 Hawkins et al.
9,198,825 B2 12/2015 Katragadda et al.
9,421,025 B2 8/2016 Hawkins et al.
9,433,428 B2 9/2016 Hakala et al.
10,118,015 B2 11/2018 De La Rama et al.
10,149,690 B2 12/2018 Hawkins et al.
10,154,799 B2 12/2018 Van Der Weide et al.
10,555,744 B2 2/2020 Nguyen et al.
10,709,462 B2 7/2020 Nguyen et al.
10,966,737 B2 4/2021 Nguyen
11,000,299 B2 5/2021 Hawkins et al.
11,337,713 B2 5/2022 Nguyen et al.
11,478,261 B2 10/2022 Nguyen
11,534,187 B2 12/2022 Bonutti
11,596,423 B2 3/2023 Nguyen et al.
12,426,938 B2 * 9/2025 Vo ...................... A61B 17/2202
2001/0044596 A1 11/2001 Jaafar
2002/0045890 A1 4/2002 Celliers et al.
2002/0082553 A1 6/2002 Duchamp
2002/0177889 A1 11/2002 Brisken et al.

(56) References Cited

U.S. PATENT DOCUMENTS

| | | | | |
|---|---|---|---|---|
| 2003/0004434 | A1 | 1/2003 | Greco et al. | |
| 2003/0176873 | A1 | 9/2003 | Chernenko et al. | |
| 2003/0229370 | A1 | 12/2003 | Miller | |
| 2004/0006333 | A1 | 1/2004 | Arnold et al. | |
| 2004/0010249 | A1 | 1/2004 | Truckai et al. | |
| 2004/0044308 | A1 | 3/2004 | Naimark et al. | |
| 2004/0097963 | A1 | 5/2004 | Seddon | |
| 2004/0097996 | A1 | 5/2004 | Rabiner et al. | |
| 2004/0162508 | A1 | 8/2004 | Uebelacker | |
| 2004/0249401 | A1 | 12/2004 | Rabiner et al. | |
| 2004/0254570 | A1 | 12/2004 | Hadjicostis et al. | |
| 2005/0015953 | A1 | 1/2005 | Keidar | |
| 2005/0021013 | A1 | 1/2005 | Visuri et al. | |
| 2005/0059965 | A1 | 3/2005 | Eberl et al. | |
| 2005/0075662 | A1 | 4/2005 | Pedersen et al. | |
| 2005/0090888 | A1 | 4/2005 | Hines et al. | |
| 2005/0113722 | A1 | 5/2005 | Schultheiss | |
| 2005/0113822 | A1 | 5/2005 | Fuimaono et al. | |
| 2005/0171527 | A1 | 8/2005 | Bhola | |
| 2005/0228372 | A1 | 10/2005 | Truckai et al. | |
| 2005/0245866 | A1 | 11/2005 | Azizi | |
| 2005/0251131 | A1 | 11/2005 | Lesh | |
| 2006/0004286 | A1 | 1/2006 | Chang et al. | |
| 2006/0069424 | A1 | 3/2006 | Acosta et al. | |
| 2006/0074484 | A1 | 4/2006 | Huber | |
| 2006/0184076 | A1 | 8/2006 | Gill et al. | |
| 2006/0190022 | A1 | 8/2006 | Beyar et al. | |
| 2006/0221528 | A1 | 10/2006 | Li et al. | |
| 2007/0016112 | A1 | 1/2007 | Schultheiss et al. | |
| 2007/0088380 | A1 | 4/2007 | Hirszowicz et al. | |
| 2007/0129667 | A1 | 6/2007 | Tiedtke et al. | |
| 2007/0156129 | A1 | 7/2007 | Kovalcheck | |
| 2007/0239082 | A1 | 10/2007 | Schultheiss et al. | |
| 2007/0239253 | A1 | 10/2007 | Jagger et al. | |
| 2007/0244423 | A1 | 10/2007 | Zumeris et al. | |
| 2007/0250052 | A1 | 10/2007 | Wham | |
| 2007/0255270 | A1 | 11/2007 | Carney | |
| 2007/0282301 | A1 | 12/2007 | Segalescu et al. | |
| 2007/0299481 | A1 | 12/2007 | Syed et al. | |
| 2008/0097251 | A1 | 4/2008 | Babaev | |
| 2008/0188913 | A1 | 8/2008 | Stone et al. | |
| 2009/0041833 | A1 | 2/2009 | Bettinger et al. | |
| 2009/0171278 | A1* | 7/2009 | Hirszowicz | A61M 25/104 604/509 |
| 2009/0227992 | A1 | 9/2009 | Nir et al. | |
| 2009/0230822 | A1 | 9/2009 | Kushculey et al. | |
| 2009/0247945 | A1 | 10/2009 | Levit et al. | |
| 2009/0254114 | A1 | 10/2009 | Hirszowicz et al. | |
| 2009/0299447 | A1 | 12/2009 | Jensen et al. | |
| 2010/0016862 | A1 | 1/2010 | Hawkins et al. | |
| 2010/0036294 | A1 | 2/2010 | Mantell et al. | |
| 2010/0094209 | A1 | 4/2010 | Drasler et al. | |
| 2010/0114020 | A1 | 5/2010 | Hawkins et al. | |
| 2010/0114065 | A1 | 5/2010 | Hawkins et al. | |
| 2010/0121322 | A1 | 5/2010 | Swanson | |
| 2010/0179424 | A1 | 7/2010 | Warnking et al. | |
| 2010/0286709 | A1 | 11/2010 | Diamant et al. | |
| 2010/0305565 | A1 | 12/2010 | Truckai et al. | |
| 2011/0034832 | A1 | 2/2011 | Cioanta et al. | |
| 2011/0118634 | A1 | 5/2011 | Golan | |
| 2011/0208185 | A1 | 8/2011 | Diamant et al. | |
| 2011/0257523 | A1 | 10/2011 | Hastings et al. | |
| 2011/0295227 | A1 | 12/2011 | Hawkins et al. | |
| 2012/0071889 | A1 | 3/2012 | Mantell et al. | |
| 2012/0095461 | A1 | 4/2012 | Herscher et al. | |
| 2012/0116289 | A1 | 5/2012 | Hawkins et al. | |
| 2012/0143177 | A1 | 6/2012 | Avitall et al. | |
| 2012/0157991 | A1 | 6/2012 | Christian | |
| 2012/0203255 | A1 | 8/2012 | Hawkins et al. | |
| 2012/0253358 | A1 | 10/2012 | Golan et al. | |
| 2013/0030431 | A1 | 1/2013 | Adams | |
| 2013/0041355 | A1 | 2/2013 | Heeren et al. | |
| 2013/0116714 | A1 | 5/2013 | Adams et al. | |
| 2013/0123694 | A1 | 5/2013 | Subramaniyan et al. | |
| 2013/0150874 | A1 | 6/2013 | Kassab | |
| 2013/0253622 | A1 | 9/2013 | Hooven | |
| 2014/0005576 | A1 | 1/2014 | Adams et al. | |
| 2014/0046229 | A1 | 2/2014 | Hawkins et al. | |
| 2014/0214061 | A1 | 7/2014 | Adams et al. | |
| 2015/0320432 | A1 | 11/2015 | Adams | |
| 2016/0151081 | A1 | 6/2016 | Adams et al. | |
| 2016/0324534 | A1 | 11/2016 | Hawkins et al. | |
| 2017/0135709 | A1 | 5/2017 | Nguyen et al. | |
| 2017/0311965 | A1 | 11/2017 | Adams | |
| 2018/0153568 | A1* | 6/2018 | Kat-Kuoy | A61B 17/22022 |
| 2019/0159792 | A1* | 5/2019 | Panian | A61M 25/104 |
| 2021/0085383 | A1 | 3/2021 | Vo et al. | |
| 2021/0338258 | A1 | 11/2021 | Hawkins et al. | |
| 2022/0240958 | A1 | 8/2022 | Nguyen et al. | |
| 2022/0313359 | A1 | 10/2022 | Schultheis et al. | |
| 2023/0107690 | A1 | 4/2023 | Nguyen | |
| 2023/0165598 | A1 | 6/2023 | Nguyen et al. | |
| 2023/0241360 | A1* | 8/2023 | Foy | A61B 17/1214 606/214 |
| 2023/0248376 | A1* | 8/2023 | Anderson | A61M 25/104 |
| 2024/0260982 | A1* | 8/2024 | Peterson | A61B 17/00234 |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 219594731 | U | 8/2023 |
| DE | 3038445 | A1 | 5/1982 |
| DE | 202006014285 | U1 | 12/2006 |
| EP | 0442199 | A2 | 8/1991 |
| EP | 0571306 | A1 | 11/1993 |
| EP | 623360 | A1 | 11/1994 |
| EP | 0647435 | A1 | 4/1995 |
| EP | 2253884 | A1 | 11/2010 |
| EP | 2362798 | B1 | 4/2014 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |

(56) References Cited

FOREIGN PATENT DOCUMENTS

| | | | |
|---|---|---|---|
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2019099218 | A1 | 5/2019 |
| WO | WO-2023113800 | A1 | 6/2023 |

OTHER PUBLICATIONS

Unpublished U.S. Appl. No. 18/524,575 (Hasenberg et al.), filed Nov. 30, 2023, titled "Systems, Devices, and Methods for Generating Shock Waves in a Forward Direction," (Copy not submitted herewith pursuant to the waiver of 37 C.F.R. § 1.98(a)(2)(iii)).

Unpublished U.S. Appl. No. 18/680,853 (Peng et al.), filed May 31, 2024, titled "Laser Intravasular Lithotripsy Device for Stenosis Calcified Lesions," (Copy not submitted herewith pursuant to the waiver of 37 C.F.R. § 1.98(a)(2)(iii)).

International Search Report received for International Patent Application No. PCT/US2024/052530, mailed on Feb. 7, 2025, 10 pages.

* cited by examiner

SHOCK WAVE CATHETER WITH DIFFERENTLY SIZED SHOCK WAVE EMITTERS

CROSS-REFERENCE TO RELATED APPLICATIONS

This application claims the benefit of U.S. Provisional Patent Application No. 63/592,502, filed Oct. 23, 2023, the entire contents of which are hereby incorporated by reference herein.

FIELD OF THE DISCLOSURE

The present disclosure relates generally to the field of medical devices and methods, and more specifically to acoustic energy generating assemblies for inclusion in catheter devices used for treating lesions in a body lumen, such as calcified lesions and occlusions in vasculature.

BACKGROUND

Calcified lesions in body lumens can negatively impact patient health. For example, when calcium builds up in the walls of the coronary arteries, the calcification can restrict blood flow to the heart muscle, which can eventually lead to a heart attack. Catheter devices are one type of device that can be used to treat calcified lesions in a body lumen. When treating lesions with a catheter device, it is important to minimize damage to surrounding soft tissues while still breaking up the lesion as much as possible.

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (e.g., using a relatively low pressure of 2-4 atm) so that the balloon expands to contact the lesion but not to a degree that substantively displaces the lesion. Voltage pulses can then be applied across the electrodes of electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can include electrodes disposed within a closed volume other than an angioplasty balloon, such as a cap, balloons of variable compliancy, or other type of enclosure.

In particular, a slimmer profile at the distal end of the catheter may be desired for improved deliverability and navigability. However, greatly reducing the distal end profile may negatively affect performance, such as sonic output uniformity along a length of an IVL catheter's treatment region, which is generally preferred for shock wave devices.

SUMMARY

According to aspects of the disclosure, a catheter for treating a lesion in a body lumen includes: an elongate member extending from a proximal region of the catheter to a distal region of the catheter; a distal shock wave emitter having a distal outer diameter and located at the distal region of the catheter; a proximal shock wave emitter having a proximal outer diameter greater than the distal outer diameter and located proximally of the distal shock wave emitter, and an enclosure. The enclosure may include: a central region surrounding the distal shock wave emitter and the proximal shock wave emitter; a proximal region proximal of the central region and having a proximal leg portion and a proximal tapering portion connecting the proximal region and the central region; and a distal region distal of the central region and having a distal leg portion and a distal tapering portion connecting the distal region and the central region. The enclosure, in some embodiments, is an angioplasty balloon.

The difference between the distal outer diameter and the proximal outer diameter may be at least 0.001 inch (0.0254 mm).

The difference between the distal outer diameter and proximal outer diameter may be least 0.0015 inch (0.0381 mm).

The distal outer diameter may be at most 98% of the proximal outer diameter.

The distal outer diameter may be at most 97.5% of the proximal outer diameter.

A longitudinal distance from a center of the distal shock wave emitter to a center of the proximal shock wave emitter may be at least 6 mm.

The longitudinal distance from the center of the distal shock wave emitter to the center of the proximal shock wave emitter may be at least 7 mm.

The distal shock wave emitter may include a distal electrode pair, and the proximal shock wave emitter may include a proximal electrode pair.

The distal electrode pair may include a distal outer electrode and a distal inner electrode, and the proximal electrode pair may include a proximal outer electrode and a proximal inner electrode. An outer diameter of the distal outer electrode may be less than an outer diameter of the proximal outer electrode.

The distal shock wave emitter and the proximal shock wave emitter may be independently wired to a voltage pulse generator. The distal shock wave emitter may be electrically connected to a distal conductor. The proximal shock wave emitter may be electrically connected to a proximal conductor. One or more return conductors may be connected to one or both of the shock wave emitters. One or more of the conductors may include a conductive wire.

The catheter may further include a distal conductor that extends from a voltage pulse generator to the distal shock wave emitter and a proximal conductor that extends from the voltage pulse generator to the proximal shock wave emitter and not the distal shock wave emitter.

The catheter may further include an intermediate shock wave emitter having an intermediate outer diameter greater than the distal outer diameter and less than the proximal outer diameter and located proximally of the distal shock wave emitter.

The catheter may include four distal shock wave emitters and four proximal shock wave emitters.

The catheter may include two proximal shock wave emitters and a single distal shock wave emitter.

When the enclosure is filled with a fluid to a pressure between 0.5 atm and 5 atm, the central region may taper in diameter. The fluid may include a saline solution, a fluoroscopic contrast solution, or a mixture of saline and contrast solution.

According to aspects of the disclosure, a shock wave catheter for treating a lesion in a body lumen with shock waves includes: an elongate member extending from a proximal region of the catheter to a distal region of the catheter; a plurality of shock wave emitters located at the distal region of the catheter; and an enclosure. The enclosure may include: a distal portion; a proximal portion; and a central portion located between the distal portion and the proximal portion and surrounding the plurality of shock wave emitters. In a first configuration, the enclosure is substantially collapsed, and a proximal outer diameter of the catheter at a proximal side of the central portion may be greater than a distal outer diameter of the catheter at a distal side of the central portion. In a second configuration, the enclosure is inflated with a fluid, and the proximal outer diameter of the catheter may be less than the distal outer diameter.

In the first configuration, the difference between the distal outer diameter and the proximal outer diameter may be at least 0.2 mm.

In the first configuration, the difference between the distal outer diameter and proximal outer diameter may be at least 0.4 mm.

In the first configuration, the distal outer diameter may be no greater than 98% of the proximal outer diameter.

In the first configuration, the distal outer diameter may be no greater than 97.5% of the proximal outer diameter.

The plurality of shock wave emitters may further include a proximal shock wave emitter and a distal shock wave emitter, wherein a longitudinal distance from a center of the distal shock wave emitter to a center of the proximal shock wave emitter is no less than 6 mm.

The longitudinal distance from the center of the distal shock wave emitter to the center of the proximal shock wave emitter may be at least than 7 mm.

The distal shock wave emitter may include a distal electrode pair and the proximal shock wave emitter may include a proximal electrode pair.

The distal electrode pair may include a distal outer electrode and a distal inner electrode and the proximal electrode pair may include a proximal outer electrode and a proximal inner electrode. An outer diameter of the distal outer electrode may be less than an outer diameter of the proximal outer electrode.

The distal shock wave emitter and the proximal shock wave emitter may be independently wired to a voltage pulse generator.

The plurality of shock wave emitters may include four distal shock wave emitters and four proximal shock wave emitters.

According to aspects of the disclosure, a shock wave catheter includes: an elongate member extending form a proximal region of the catheter to a distal region of the catheter; a distal shock wave emitter including a distal inner band and a distal outer band having a distal outer diameter; and a proximal shock wave emitter including a proximal inner band and a proximal outer band having a proximal outer diameter greater than the distal outer diameter.

The distal inner band may be thinner than the proximal inner band.

The distal inner band may have the same thickness as the proximal inner band.

The distal shock wave emitter may include a distal insulative layer, the proximal shock wave emitter may include a proximal insulative layer, and the distal insulative layer may be thinner than the proximal insulative layer.

The distal shock wave emitter may include a distal insulative layer, the proximal shock wave emitter may include a proximal insulative layer, and the distal insulative layer may be the same thickness as the proximal insulative layer.

DESCRIPTION OF THE FIGURES

Illustrative aspects of the present disclosure are described in detail below with reference to the following figures. It is intended that the embodiments and figures disclosed herein are to be considered illustrative and exemplary rather than restrictive.

DETAILED DESCRIPTION

Figure 1:
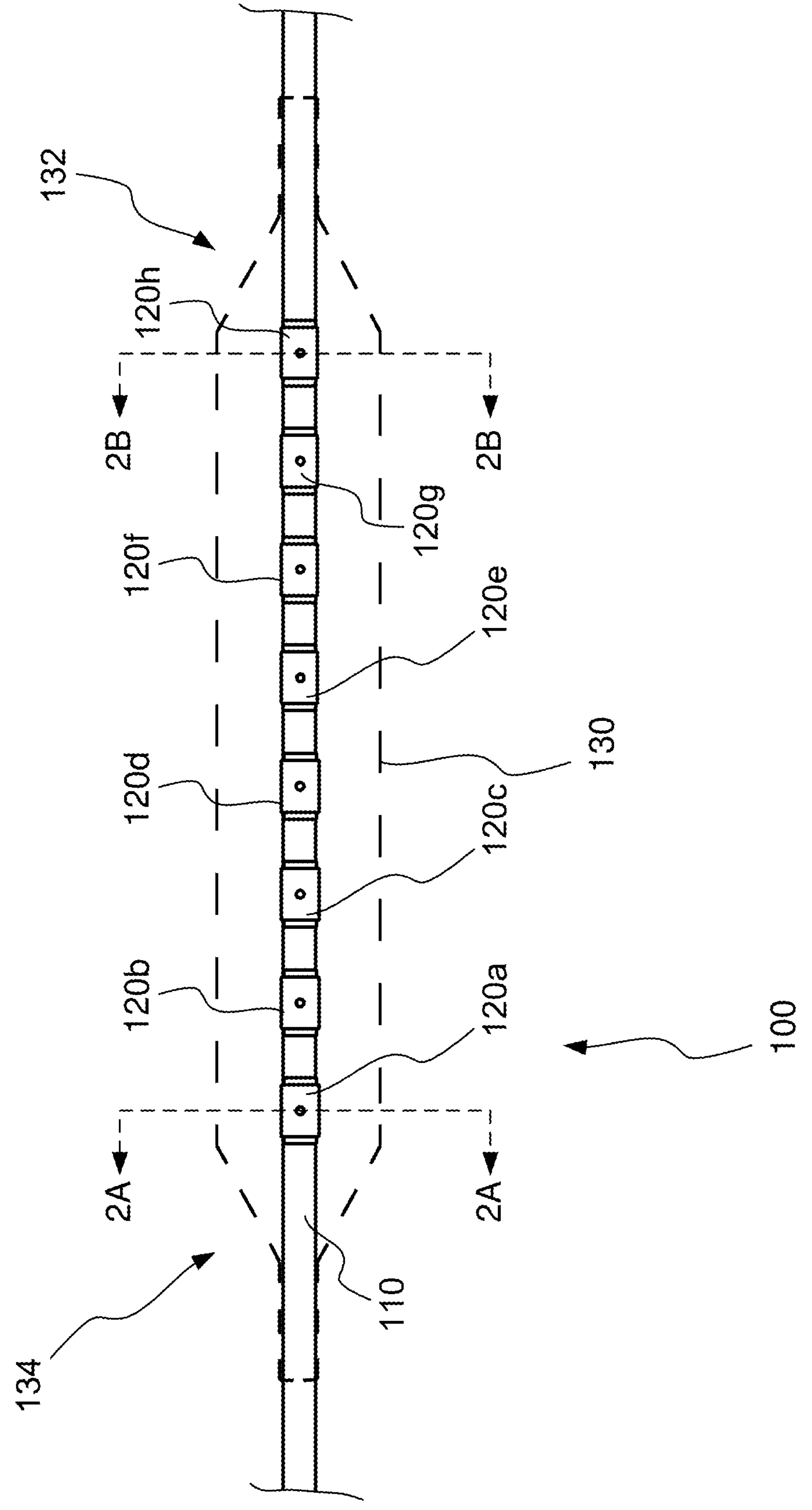
FIG. 1 illustrates a distal region of shock wave catheter for treating a lesion in a body lumen, according to some embodiments.

The following description is presented to enable a person of ordinary skill in the art to make and use the various embodiments and aspects thereof disclosed herein. Descriptions of specific catheters, systems, methods, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement. Furthermore, numerical designators such as “first,” “second,” “third,” “fourth,” etc. are merely descriptive and do not indicate a relative order, location, or identity of elements or features described by the designators. For instance, a “first” shock wave may be immediately succeeded by a “third” shock wave, which is then succeeded by a “second” shock wave. As another example, a “third” emitter may be used to generate a “first” shock wave and vice versa. Accordingly, numerical designators of various elements and features are not intended to limit the disclosure and may be modified and interchanged.

In addition, it is also to be understood that the singular forms “a,” “an,” and “the” used in the following description are intended to include the plural forms as well, unless the context clearly indicates otherwise. It is also to be understood that the term “and/or” as used herein refers to and encompasses any and all possible combinations of one or more of the associated listed items. It is further to be understood that the terms “includes,” “including,” “comprises,” and/or “comprising,” when used herein, specify the presence of stated features, integers, steps, operations, elements, components, and/or units but do not preclude the presence or addition of one or more other features, integers, steps, operations, elements, components, units, and/or groups thereof.

As used herein, the term “electrode” refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term “electrode pair” refers to two electrodes that are positioned adjacent to each other such that application of a sufficiently high voltage to the electrode pair will cause an electrical current to transmit across the gap (also referred to as a “spark gap”) between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term “emitter” broadly refers to the region of an electrode assembly where the current transmits across the electrode pair, generating a shock wave. The term “emitter sheath” or “emitter band” (which are used interchangeably) refers to a sheath/band of conductive material that may form one or more electrodes of one or more electrode pairs, thereby forming a location of one or more emitters.

Components of emitters, including electrodes and emitter sheaths/bands, may be formed from a metal, such as stainless steel, copper, tungsten, platinum, palladium, molybdenum, cobalt, chromium, iridium, an alloy or alloys thereof, such as cobalt-chromium, platinum-chromium, cobalt-chromium-platinum-palladium-iridium, or platinum-iridium, or a mixture of such materials.

In some embodiments, an IVL catheter is a so-called “rapid exchange-type” (“Rx”) catheter provided with an opening portion through which a guide wire is guided (e.g., through a middle portion of a central tube in a longitudinal direction). In other embodiments, an IVL catheter may be an “over-the-wire-type” (“OTW”) catheter in which a guide wire lumen is formed throughout the overall length of the catheter, and a guide wire is guided through the proximal end of a hub.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, 9,433,428, and 10,709,462, in U.S. Publication No. 2021/0085383, and in U.S. patent application Ser. No. 18/586,299, all of which are incorporated herein by reference in their entireties. Other catheter designs have improved the delivery of shock waves, for instance, by specific electrode construction and configuration thereby directing shock waves in a forward direction to break up tighter and harder-to-cross occlusions in vasculature. Examples of forward-biased or firing-firing catheter designs can be found in U.S. Pat. Nos. 10,966,737, 11,478,261, and 11,596,423, in U.S.

Publication Nos. 2023/0107690 and 2023/0165598, and in U.S. patent application Ser. Nos. 18/524,575 and 18/680,853, all of which are incorporated herein by reference in their entireties.

FIG. 1 illustrates a distal region of shock wave catheter 100 for treating a lesion in a body lumen, according to some embodiments of the present disclosure. Shock wave catheter 100 includes an elongate member 110 that extends from a proximal region to a distal region of shock wave catheter 100, although only a portion of the elongate member 110 is shown in FIG. 1. Shock wave catheter 100 further includes a plurality of shock wave emitters 120*a*-120*h* that are located along the elongate member 110. Shock wave emitters 120*a*-120*h* are enclosed within enclosure 130, which may be a balloon, for example. Enclosure 130 includes a distal side 132 and a proximal side 134.

As used herein, the terms "distal" and "proximal" are used to refer to opposing directions relative to the distal and proximal ends of a catheter. The distal end of the catheter is advanced through a body lumen (e.g., blood vessel) to a treatment site and extends from a proximal end, which may include a fluid port and a power port for supplying fluid and power to the treatment site.

Shock wave emitters 120*a*-120*d* are located on a proximal side of balloon 130 and shock wave emitters 120*e*-120*h* are located on a distal side of balloon 130. In various embodiments, distal shock wave emitters 120*e*-120*h* are differently sized and/or shaped from proximal shock wave emitters 120*a*-120*d* to provide more flexibility and/or a narrower overall profile at the distal end of the device. For example, distal shock wave emitters 120*e*-120*h* may have a smaller outer diameter than proximal shock wave emitters 120*a*-120*d*. In other embodiments, only the two most distal emitters 120*g* and 120*h* have a smaller outer diameter.

Shock wave emitters 120*a*-120*h* may be spaced apart from each other optimize sonic output uniformity. In one or more embodiments, adjacent shock wave emitters are spaced apart by a distance no less than 4 mm away from each other. In some embodiments, adjacent shock wave emitters may be spaced apart by a distance no less than 6 mm away from each other. In some embodiments, adjacent shock wave emitters may be spaced apart by a distance no less than 7 mm away from each other. In some embodiments, adjacent shock wave emitters may be spaced apart by a distance no less than 10 mm away from each other. Herein, distance between emitters is measured along a longitudinal direction (i.e., proximal to distal direction) from a midpoint of one emitter to a midpoint of another emitter.

In some embodiments, a distance between adjacent emitters may be chosen to promote constructive interference from generated shock waves. For example, a distance between adjacent emitters may be no less than 1 mm and no more than 4 mm.

In some embodiments, a distance between adjacent emitters may be chosen to provide a higher sonic output at certain regions of the catheter. For example, in FIG. 1, emitters 120*d* and 120*e* may be spaced closer together than other adjacent emitters of catheter 100. By spacing emitters 120*d* and 120*e* closer together, sonic pressure may be higher at a central region of the enclosure 130. In some examples, more than two emitters may be spaced closer together to promote constructive interference of shock waves generated at the more than two emitters.

Figure 2B:
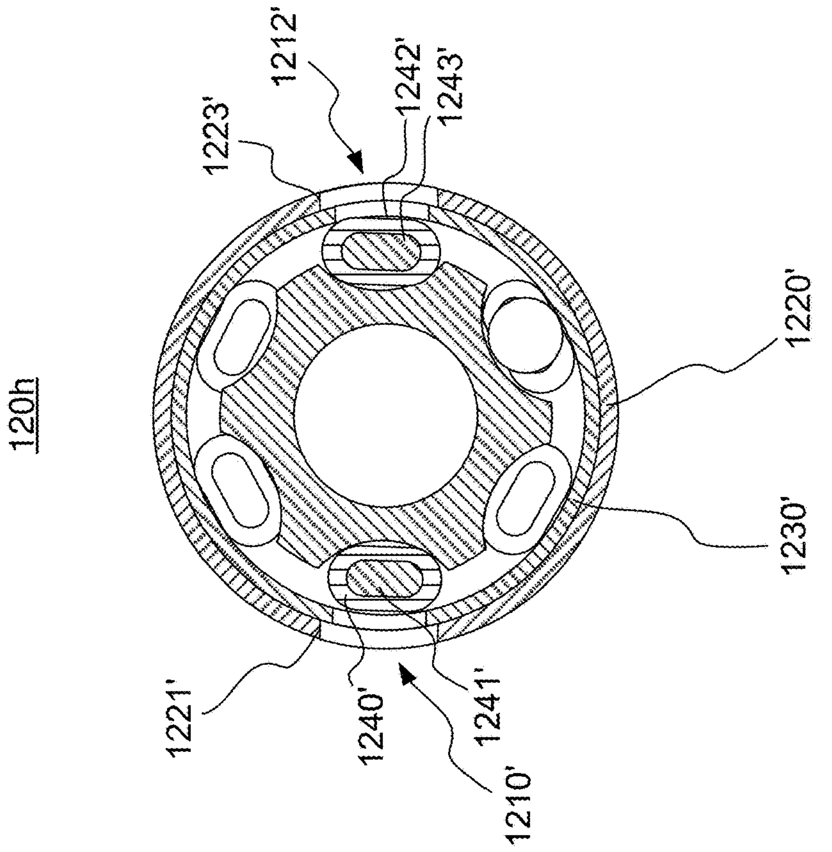
FIGS. 2A and 2B illustrate cross-sectional views of a proximal emitter and a distal emitter, respectively, according to some embodiments.
Figure 2A:
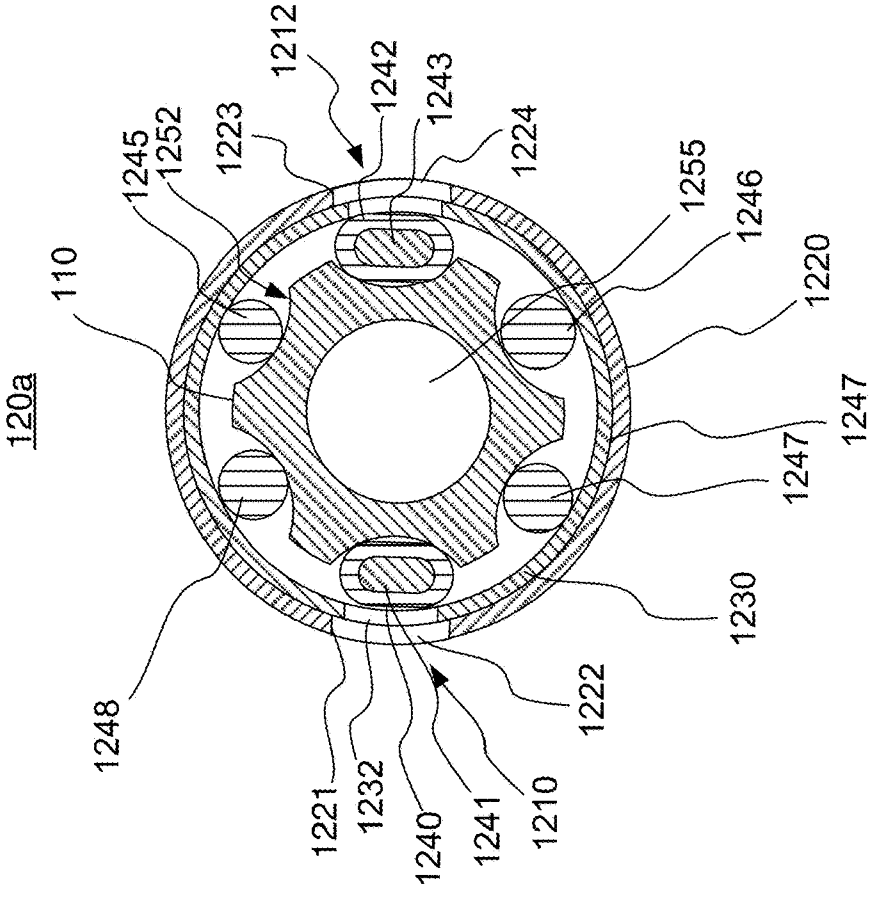
Figure 3B:
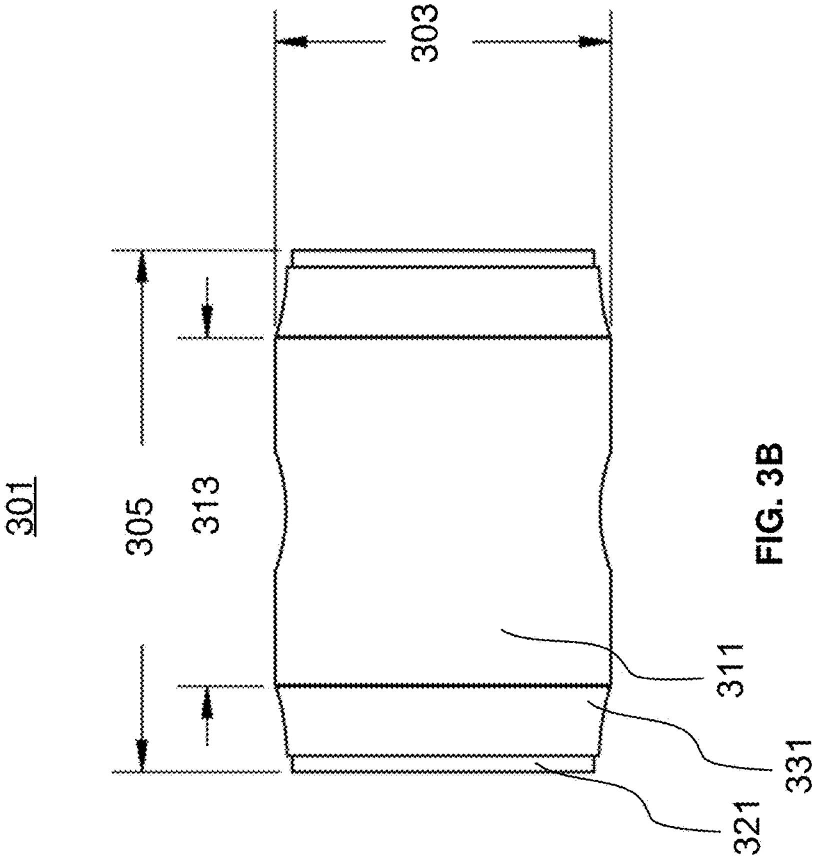
FIGS. 3A and 3B illustrate parts of a proximal emitter and a distal emitter, respectively, according to some embodiments.
Figure 3A:
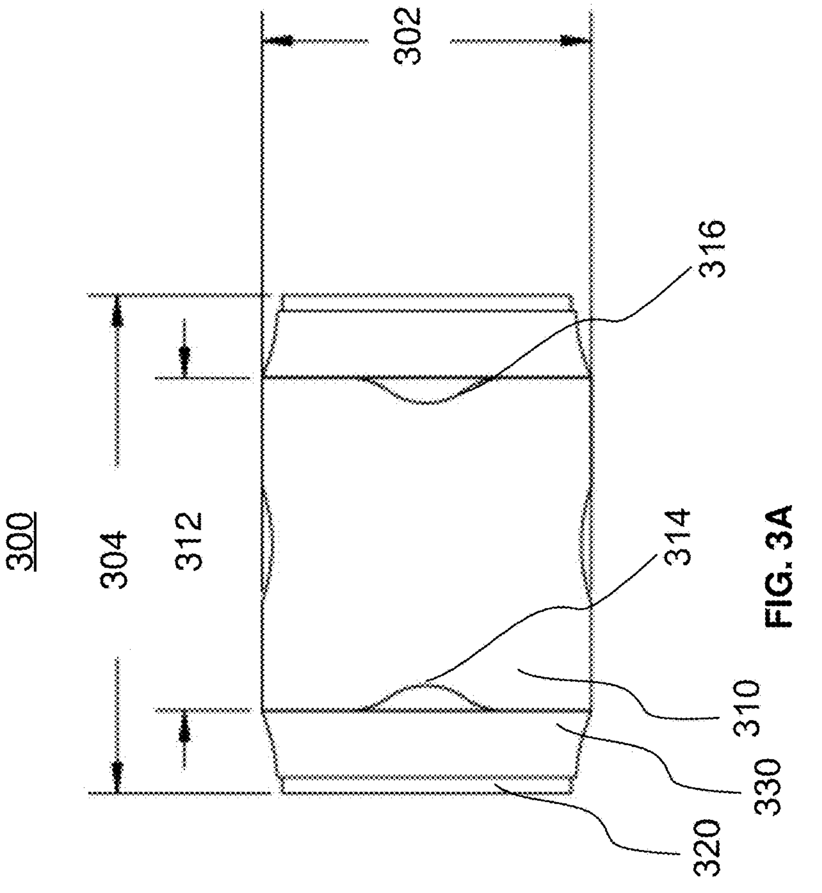

FIGS. 2A and 2B illustrate cross-sectional views of proximal emitter 120*a* at plane 2A-2A and distal emitter 120*h* at plane 2B-2B, respectively, according to some aspects of the disclosure. FIGS. 3A and 3B illustrate side views of proximal emitter 120*a* and distal emitter 120*h*, respectively. Proximal emitter 120*a* includes an outer band 1220 that at least partially surrounds an insulating layer 1230. Outer band 1220 may include openings 1222 and 1224 and the insulating layer 1230 may include openings 1232 and 1234 that are at least partially aligned with outer band openings 1222 and 1224. The inner edges of outer band openings 1222 and 1224 may form outer electrodes 1221 and 1223. Insulating layer 1230 at least partially surrounds inner electrodes 1240 and 1242. Outer electrode 1221 and inner electrode 1240 form electrode pair 1210. Outer electrode 1223 and inner electrode 1242 form electrode pair 1212. Inner electrodes 1240 and 1242 may be electrically connected (e.g., by crimping) to electrical wires 1241 and 1243. The electrical wires 1241 and 1243 in turn may extend proximally along elongate member 110 to the proximal end of the catheter 100 or distally along elongate member 110 to an adjacent emitter. Elongate member 110 may have one or more elongate grooves (e.g., groove 1252) along which wires may extend. In other embodiments, an elongate member may have one or more wire lumens. Elongate member 1250 includes central lumen 1255, which may be used for delivering catheter 100 along a guide wire to the treatment site.

When a voltage pulse is applied to proximal emitter 120*a*, current may be delivered from a power supply to inner electrode 1240. Voltage may then be applied across the spark gap formed between inner electrode 1240 and outer electrode 1221, generating a shock wave at electrode pair 1210. The current may further be delivered along outer band 1220 to outer electrode 1223 and across the spark gap formed between outer electrode 1223 and inner electrode 1242, generating a shock wave at electrode pair 1212. Current may then be delivered to an adjacent emitter (e.g., emitter 120*b*). Accordingly, electrode pairs of catheter 100 may be electrically connected in series. Other electrode pairs may be separately connected to the power source, requiring separate wiring (e.g., wires 1245, 1246, 1247, or 1248).

While emitter 120*a* is illustrated as including two electrode pairs, other embodiments may include one electrode pair or three or more electrode pairs. And while electrode pairs 1210 and 1212 are shown on opposite sides of proximal emitter 120*a* in FIG. 2A, in other embodiments, electrode pairs may be concentrated substantially on one side or may be more circumferentially aligned and offset axially along the longitudinal length of an emitter. Such designs may be favored for targeting, e.g., eccentric lesions or nodular lesions.

FIG. 2A illustrates wires 1245, 1246, 1247, and 1248 that deliver electric currents to or from emitters that are distal to emitter 120*a*. In contrast, only wires 1241' and 1243' extend to emitter 120*h* as shown in cross-section of emitter 120*b*, illustrated in FIG. 2B. Since emitter 120*h* is the distalmost emitter, additional wires to deliver current to more distal emitters are not necessary. Wires 1241' and 1243' are electrically connected (e.g., by crimping) to inner electrodes 1240' and 1242', respectively. Inner electrodes 1240' and 1242' with outer electrodes 1221' and 1223' form electrode pairs 1210' and 1212', respectively.

Because the more distal emitters may not need to accommodate as many wires as the proximal emitters, some components of the more distal emitters may be made smaller to provide a more slender profile than the proximal emitters. For example, one or both of outer band 1220' and insulating layer 1230' may be made with smaller outer diameters than outer band 1220 and insulating layer 1230.

Various embodiments of the present IVL catheter may implement further sizes of emitters. For example, an exemplary IVL catheter having eight emitters may have four proximal emitters having a first diameter that is relatively larger than the next two sequentially distal emitters having a second diameter, where the second diameter of those two emitters may in turn be relatively larger than a third diameter associated with the two most distal emitters of the catheter.

Various embodiments of the present IVL catheter may implement different wire sizes. For example, wires arranged to carry current from proximal emitters to distal emitters may be smaller or thinner than wires that carry current from a power source to the proximal end of the catheter, further reducing the overall cross-sectional profile of the catheter tip region. Alternatively, different wire sizes may be selected based on the metal or alloy used for the wires. In further implementations, different wires sizes, thicker or thinner, may be used leading to or in between emitters in order to manage the current delivered to a given emitter through the resistivity of the wire.

It should be understood that further numbers of emitters, wiring and size variations, and wiring and size combinations of emitter diameter sizing along the length of an IVL catheter are within the scope of this disclosure.

While catheter 100 is shown with eight shock wave emitters, other IVL catheter embodiments may include fewer or more shock wave emitters. For example, in applications requiring shorter angioplasty balloons, only two shock wave emitters may be necessary and the distal emitter may be designed with a smaller profile than the proximal emitter. In other relatively short balloon embodiments having three shock wave emitters, one implementation can have one distal emitter with a smaller profile than two proximal emitters, while an implementation in the alternative can have two distal emitters with a smaller profile than one proximal emitter.

In another embodiment, an IVL catheter may include two shock wave emitters with a proximal emitter that has a larger outer diameter than a distal emitter.

In another embodiment, an IVL catheter may include nine shock wave emitters. In such an application, to deliver sufficiently uniform and high energy, one or some of the shock wave emitters may be wired to separate electrical channels. For example, in a nine-shock wave emitter catheter, three of the most proximal emitters may be wired in series together, three of the middle emitters may be wired in series together, and three of the most distal emitters may be wired in series together. In some embodiments, the three most distal emitters have a smaller profile than the other six emitters. In other embodiments, the six most distal emitters have a smaller profile than the other three emitters.

FIGS. 3A and 3B illustrate parts of a proximal emitter 300 and a distal emitter 301, respectively. Proximal emitter 300 is located more proximally along an elongate member (e.g., elongate member 110) than distal emitter 301. Proximal emitter 300 includes an outer band 310 and insulating layer 320. The outer band 310 may be adhered to the insulating layer 320 with an adhesive 330. Similarly, distal emitter includes an outer band 311 and insulating layer 321. The outer band 311 may be adhered to the insulating layer 321 with an adhesive 331.

According to some embodiments, proximal emitter 300 includes a proximal emitter outer diameter 302. Distal emitter 301 has a distal emitter outer diameter 303 that is less than proximal emitter outer diameter 302. In some embodiments, distal emitter outer diameter 303 is at least 0.0005 inch (0.0127 mm) less than proximal emitter outer diameter 302. In some embodiments, distal emitter outer diameter 303 is at least 0.001 inch (0.0254 mm) less than proximal emitter outer diameter 302. In some embodiments, distal emitter outer diameter 303 is at least 0.0015 inch (0.0381 mm) less than proximal emitter outer diameter 302. In some embodiments, distal emitter outer diameter 303 is no more than 0.04 inch (1.02 mm). In some embodiments, distal emitter outer diameter 303 is no more than 0.0395 inch (1.00 mm). In some examples, distal emitter outer diameter 303 is no greater than 98% of the proximal emitter outer diameter 302. In some examples, distal emitter outer diameter 303 is no greater than 97.5% of the proximal emitter outer diameter 302. Note that in these embodiments, proximal emitter outer diameter 302 corresponds to the outer diameter of proximal outer band 310, and the distal emitter outer diameter 303 corresponds to the outer diameter of the distal outer band 311.

To achieve a slimmer profile, one or both of the outer band 311 and insulating layer 321 of distal emitter 301 have a smaller outer diameter than outer band 310 and insulating layer 320 of the proximal emitter 300. In some embodiments, one or both of the outer band 311 and insulating layer 321 have smaller inner diameters than outer band 310 and insulating layer 320. Additionally or alternatively, one or more of the layers of the distal emitter 301 (e.g., outer band 311 or insulating layer 321) may be thinner than the proximal emitter 300. In some embodiments, an elongate member (e.g., elongate member 110) of the catheter may be made thinner at the more distal regions of the catheter to provide a slimmer profile and flexibility at the distal end.

As shown in FIGS. 3A and 3B, proximal emitter 300 has a length 304 (measured in the proximal-distal direction) and distal emitter 301 has a length 305. Proximal outer band 310 has a length 312 and distal outer band has a length 313. In some embodiments, one or both of proximal emitter length 304 and proximal outer band length 312 are greater than distal emitter length 305 and distal outer band length 313, respectively. These features may provide additional flexibility and navigability at the distal end of a shock wave catheter.

Proximal emitter 300 includes notches 314 and 316 formed on outer band 310. These notches serve as visual indicators that distinguish proximal emitter 300 from distal emitter 301 during manufacturing of a shock wave catheter. Other indicia on an outer band of an emitter are possible, such as different colors, patterns, etched markings, or painted markings. In some embodiments, other features of the emitter band and insulating layer assembly may be different to serve as visual indicators that distinguish a larger outer diameter proximal emitter from a smaller outer diameter distal emitter. For example, the insulating layer (e.g., proximal insulating layer 320) of the proximal emitter assembly may be different in color from the insulating layer (e.g., distal insulating layer 321) of the distal emitter assembly. These indicia need not be formed on the proximal emitter 300 and may be formed on distal emitter 301 instead. Additionally or alternatively, the insulation on the wiring connected to the emitters may have different colors, patterns, or other such visual indicia to distinguish which wires are electrically connected to a proximal emitter 300 versus a distal emitter 301 during manufacturing of a shock wave catheter.

In some examples, a shock wave catheter includes a plurality of emitters (such as proximal emitter 300 and distal emitter 301) that have one or more components that differ in one or more dimensions such that at least one of the plurality of emitters has a smaller outer diameter than at least one other emitter. In some embodiments, the one or more dimensions may include the outer diameter of an outer band (such as outer bands 310 and 311). In some embodiments, the one or more dimensions may include a thickness of the outer band.

In some embodiments, the thickness of one or more of the outer bands may be at least 0.001 inch (0.0254 mm). In some embodiments, the thickness of one or more of the outer bands may be at least 0.0015 inch (0.0381 mm). In some embodiments, the thickness of a first outer band may be at least 0.001 inch (0.0254 mm), and the thickness of a second outer band may be greater than the thickness of the first outer band. In some embodiments, at least one outer band may have a thickness greater than or equal to 0.0005 inch (0.0127 mm). Having a minimum thickness of at least 0.0005 inch (0.0127 mm) may ensure that the outer band does not erode or split during repeated shock wave generation.

In some embodiments, the thickness of at least one of the outer bands may be no greater than 0.01 inch (0.254 mm) to ensure deliverability of the catheter to the treatment site. In some embodiments, the thickness of at least one of the outer bands may be no greater than 0.0065 inch (0.165 mm). But in some embodiments where deliverability through a small body lumen is a lesser concern, such as for treatment of structural heart lesions, at least one of the outer bands may have a thickness greater than 0.01 inch (0.254 mm).

In some embodiments, the one or more dimensions may include both the outer diameter and the thickness of the outer band. A distal emitter may have an outer band with an outer band and a thickness less than an outer band of a proximal emitter.

In some embodiments, the one or more dimensions may include a thickness of an insulation layer (such as insulating layers 320 and 321). Reducing the thickness of the insulation layer of the emitters may reduce the overall crossing profile of the catheter. A minimum thickness of the insulation layer of at least one emitter may be no less than 0.0005 inch (0.0127 mm). In some embodiments, a minimum thickness of the insulation layer of at least one emitter is no less than 0.0007 inch (0.0178 mm). A maximum thickness of the insulation layer of at least one emitter may be no greater than 0.005 inch (0.127 mm). In some embodiments, the maximum thickness of the insulation layer of at least one emitter is no greater than 0.003 inch (0.0762 mm).

The insulation layer may separate first and second electrodes (e.g., an inner electrode and an outer electrode formed by a surface of an outer band), and its thickness may define a spark gap distance. Accordingly, an emitter having a thicker insulation layer may require a higher voltage pulse to spark and generate a shock wave than an emitter having a thinner insulation layer. If the insulation layer is too thick, generating a shock wave may require an impracticably high voltage pulse. If the insulation layer is too thin, it may erode quickly and cause the emitter to fail.

Optionally, emitters having different insulation layer thicknesses may include differently sized openings in the outer bands and insulation layers to generate shock waves having similar sonic outputs. For example, a distal emitter having a thinner insulation layer may include smaller openings in its outer band and its insulation layer than a proximal emitter having a thicker insulation layer. In other words, when insulation layer thicknesses of plural emitters are varied, respective surface areas of the electrode pairs may be adjusted to offset any unwanted differences in sonic output from the emitters.

In some embodiments, a distal emitter includes an insulation layer that is thinner than an insulation layer of a proximal emitter. The distal and proximal emitters may be electrically isolated from one another such that voltage pulses can be separately delivered from a voltage pulse generator to the distal and proximal emitters. The voltage pulse generator may be configured such that pulses delivered to the distal emitter are a lower voltage than pulses delivered to the proximal emitter.

According to aspects of the disclosure, the insulation layer may include an insulative polymeric material. In some embodiments, the insulation layer includes a polyimide. In some embodiments, the insulation layer includes a thermoplastic polyurethane.

In some embodiments, the one or more dimensions may include a thickness or gauge of conductors (e.g., insulated wires) that deliver voltage pulses to the emitters. One or more conductors may include a wire having a conductive core surrounded by an insulative layer. The wire may have a thickness (i.e., an outer diameter) between 0.003 inch (0.0762 mm) to 0.015 inch (0.381 mm). The conductive core may have a thickness between 0.002 inch (0.0508) and 0.01 inch (0.254 mm). The thickness of the insulative layer may be between 0.0005 inch (0.0127 mm) and 0.015 inch (0.381 mm). In some embodiments, to provide a reduced distal emitter diameter, one or more distal emitters of a catheter may be electrically connected to one or more wires that are thinner than one or more wires that are electrically connected to one or more proximal emitters. In some embodiments, a first wire of a pair of wires that are electrically connected to one or more distal emitters may be thinner a second wire of the pair wires to further reduce emitter profile. Such an arrangement of wires may also be beneficial in ensuring even erosion of electrode materials.

Figures 4A, 4B:
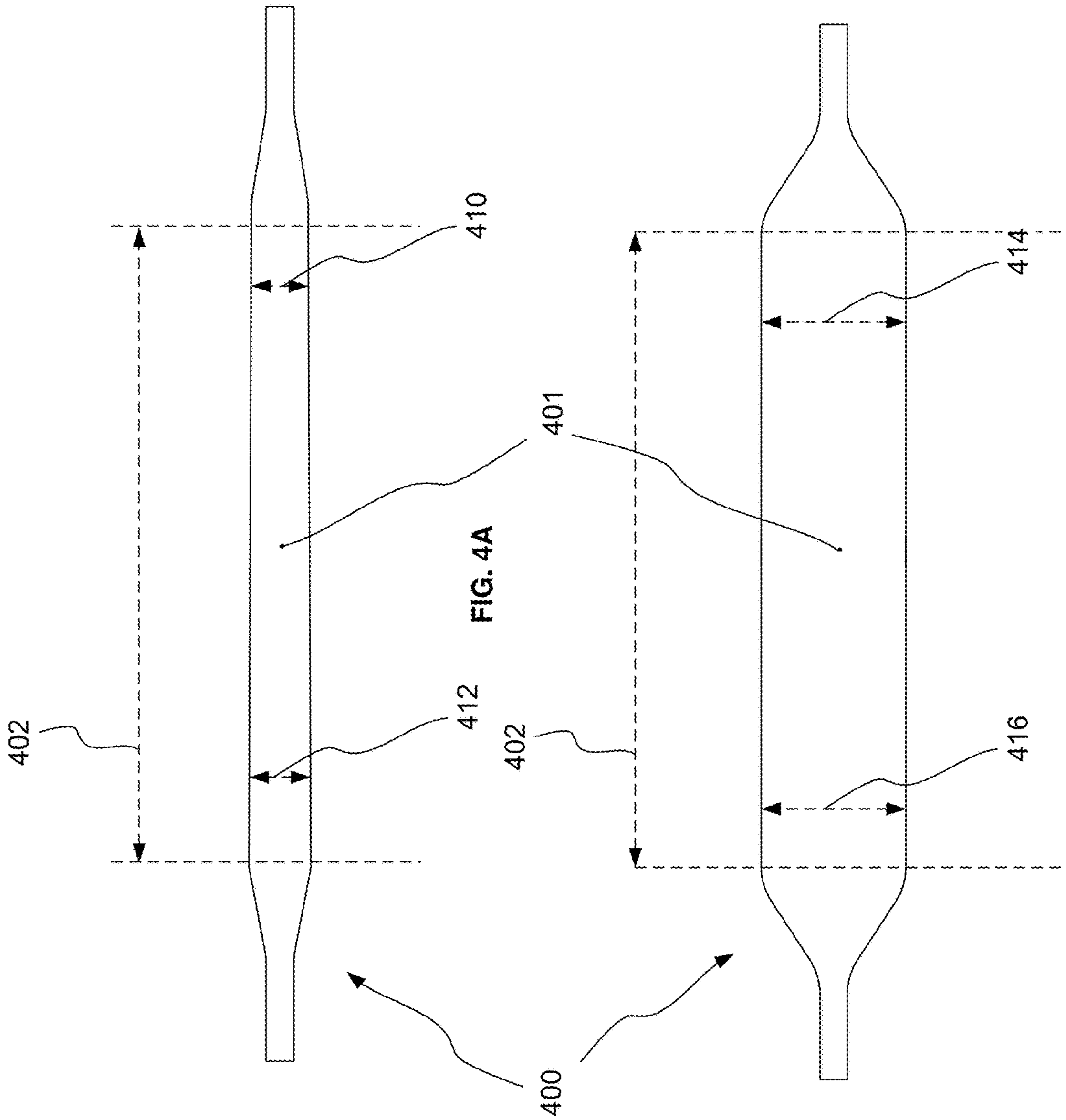
FIGS. 4A and 4B illustrate configurations for a shock wave catheter enclosure, according to some embodiments.

FIGS. 4A and 4B illustrate two configurations for shock wave catheter enclosure 400, according to one or more aspects of the disclosure. FIG. 4A illustrates enclosure 400 in a collapsed configuration, which has a smaller profile than in an expanded (e.g., inflated) configuration illustrated in FIG. 4B. But further, enclosure 400, in the collapsed configuration, has a smaller outer diameter 410 on the distal side than outer diameter 412 on the proximal side. In one or more embodiments, along enclosure 400, at locations axially aligned with shock wave emitters, the outer diameter on the distal side is smaller than on the proximal side by no less than 0.001 inch (0.0254 mm). In the expanded configuration, proximal outer diameter 416 may be substantially the same as distal outer diameter 414. In some embodiments, enclosure 400 has a substantially uniform outer diameter along its working length 402. Alternatively, in some embodiments, an enclosure has a tapering outer diameter along its working length in its expanded configuration. In some embodiments, an enclosure may have a greater outer diameter on a proximal side of the enclosure's working length than a distal side.

Here, the distal side refers to the side of the enclosure 400 distal of the enclosure center 401 and the proximal side refers to the side of the enclosure 400 proximal of the enclosure center 401. Enclosure center 401 is located at the longitudinal midpoint of the enclosure's working length 402.

Although not shown in FIG. 4A, enclosure 400 may include pleats and/or folds in a collapsed configuration. Enclosure 400 may be an angioplasty balloon. Enclosure 400 may be a semi-compliant angioplasty balloon.

During use, a shock wave catheter may be maneuvered through a body lumen (e.g., an artery) to a treatment site with the enclosure in a collapsed configuration, so it is crucial for the collapsed configuration profile to be as slim as possible, particularly at the distal end of the enclosure. When the distal region of the catheter has been delivered to the lesion, enclosure 400 is filled with fluid to a relatively low pressure (e.g., to a pressure less than 5 atm). At this inflated configuration, it may be advantageous to have a uniform outer diameter enclosure. However, depending on the size and geometry of the lesion being treated, it may be advantageous to have a non-uniform outer diameter (e.g., tapered) in the inflated configuration as described above.

Figures 5A, 5B:
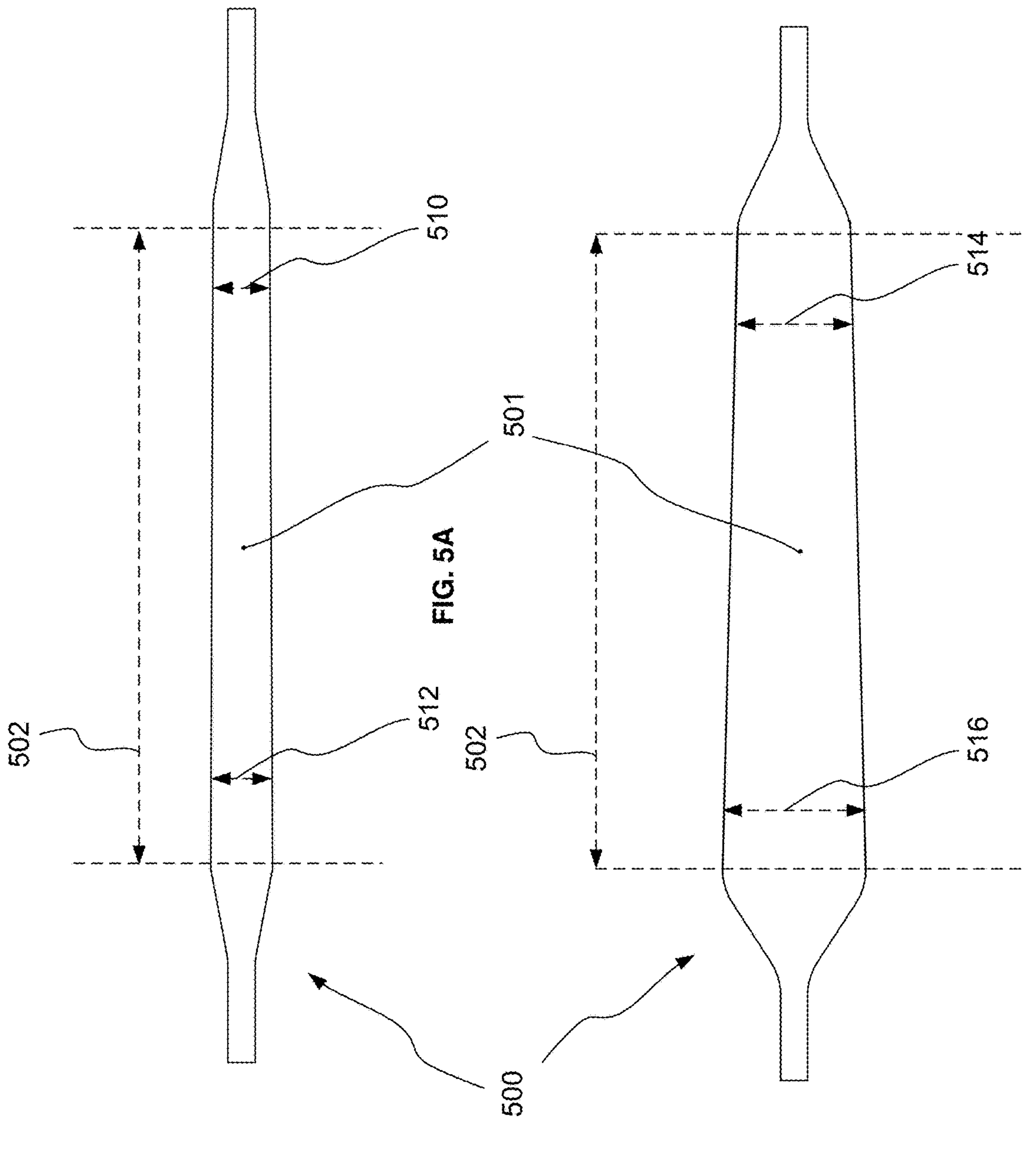
FIGS. 5A and 5B illustrate a shock wave catheter enclosure, according to some embodiments.

FIGS. 5A and 5B illustrate a shock wave catheter enclosure 500 having, along its working length 502, a proximal outer diameter 512 that is greater than a distal outer diameter 510 in a deflated configuration and a proximal outer diameter 516 that is greater than a distal outer diameter 514 in an inflated configuration, according to aspects of the disclosure. In some embodiments, enclosure 500 is an angioplasty balloon made of a semi-compliant material. In some embodiments, the proximal outer diameter 516, in the inflated configurations, is at least 0.2 mm greater than the distal outer diameter 514. In some embodiments, the proximal outer diameter 516, in the inflated configurations, is at least 0.4 mm greater than the distal outer diameter 514. In some embodiments, the distal outer diameter 514 is no greater than 98% of the proximal outer diameter 516 in the inflated configurations. In some embodiments, the distal outer diameter 514 is no greater than 97.5% of the proximal outer diameter 516 in the inflated configurations.

Here, the distal side refers to the side of the enclosure 500 distal of the enclosure center 501 and the proximal side refers to the side of the enclosure 500 proximal of the enclosure center 501. Enclosure center 501 is located at the longitudinal midpoint of the enclosure's working length 502.

In some embodiments, the outer diameter along working length 502 continuously decreases from the proximal side to the distal side. But in some embodiments, enclosure 500 may include an outer diameter that does not decrease continuously along its working length. In some embodiments, enclosure 500 may include an outer diameter that changes stepwise along its working length. Having a greater outer diameter at the proximal side than the distal side of the enclosure 500 in the inflated configuration may allow the enclosure wall to become better apposed to vessel walls of certain anatomies. For example, a tapered balloon may be employed for coronary arteries that taper and change in diameter. A tapered balloon may also be employed for carotid arteries, particularly at the transition from common carotid to internal carotid arteries. A tapered balloon may be employed for treating peripheral vessels, such as the common femoral artery, superficial femoral artery, and the popliteral artery, particularly at sections of the vessels where vessel diameter changes.

Enclosure 500 may include a plurality of shock wave emitters where at least one of the plurality of shock wave emitters has a different outer diameter than the other shock wave emitters. In some embodiments, one or more relatively larger emitters (e.g., those having a larger outer diameter emitter band) may be located at the proximal side than one or more relatively smaller emitters. By having differently sized emitters within a tapered balloon and positioning larger emitters at the proximal side of the enclosure and hence positioning the spark gaps closer to the enclosure wall, sonic output at different regions of the enclosure may be more consistent than if all of the emitters were the same size.

Figure 6:
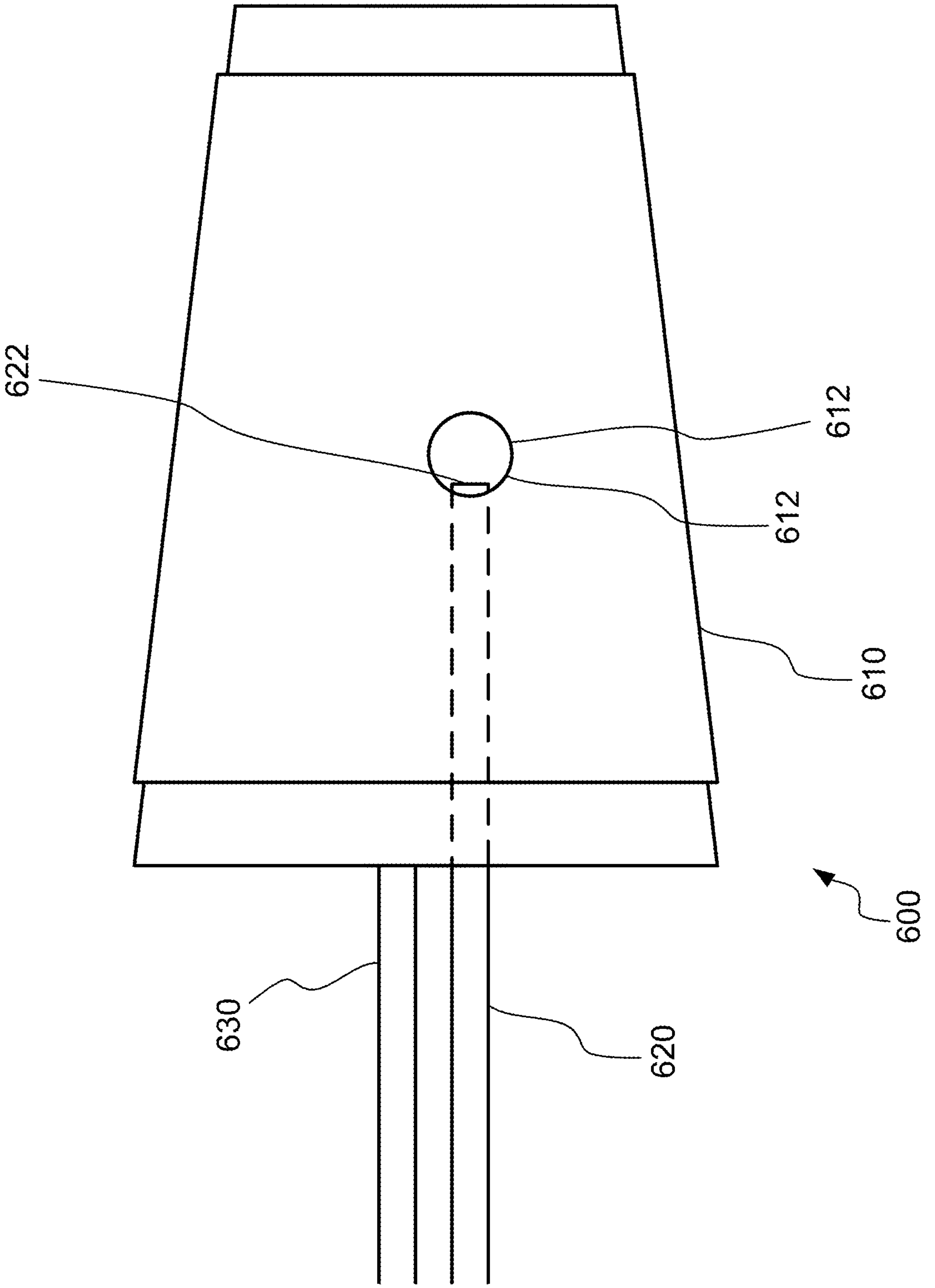
FIG. 6 illustrates a shock wave emitter that may be included as part of a shock wave catheter, according to some embodiments.

FIG. 6 illustrates a shock wave emitter 600 that may be included as part of a shock wave catheter, according to aspects of the disclosure. Shock wave emitter 600 may include an emitter band 610 that includes a conductive surface 612. Conductive surface 612 may form a first electrode of a first electrode pair. As shown in FIG. 6, conductive surface 612 may be an inner surface of an aperture 614 of emitter band 610. Emitter 600 may include a second electrode of the first electrode pair that is formed at a conductive, uninsulated surface 622 of a first conductor 620. Current from a voltage pulse may be delivered from a voltage pulse generator by conductor 620 to and across the first electrode pair generating a shock wave that propagates away from aperture 614. The current may further be delivered across a second electrode pair at the emitter 600 (not shown) generating another shock wave at the second electrode pair and return by second conductor 630 to the voltage pulse generator. In some embodiments, the second conductor may be shorted to the emitter band 610 such that shock waves are only generated at the first electrode pair. In some embodiments, rather than a conductive surface of the first conductor 620, the second electrode of the first electrode pair may be formed by another conductive surface of another conductive member that is in electrical contact with the first conductor 620. In some embodiments, a plurality of emitters, each emitter including an emitter band, are connected in series to each other such that a voltage pulse generates a shock wave at each electrode pair of the emitters connected in series. These electrical configurations may be applicable to the other emitter structures described herein.

Emitter band 610 may have a side wall where one side of emitter band 610 has a smaller outer diameter than the opposite side. In some embodiments, as shown in FIG. 6, emitter band 610 has a tapered side wall that has a smaller outer diameter on the distal side than on the proximal side. In some embodiments the proximal side of the emitter band may have a smaller outer diameter than the distal side. Tapering side walls of the emitter band, particularly those located at distal and proximal ends of the enclosure, may provide improved navigability during delivery and withdrawal of the catheter to and from the treatment site.

Figure 7:
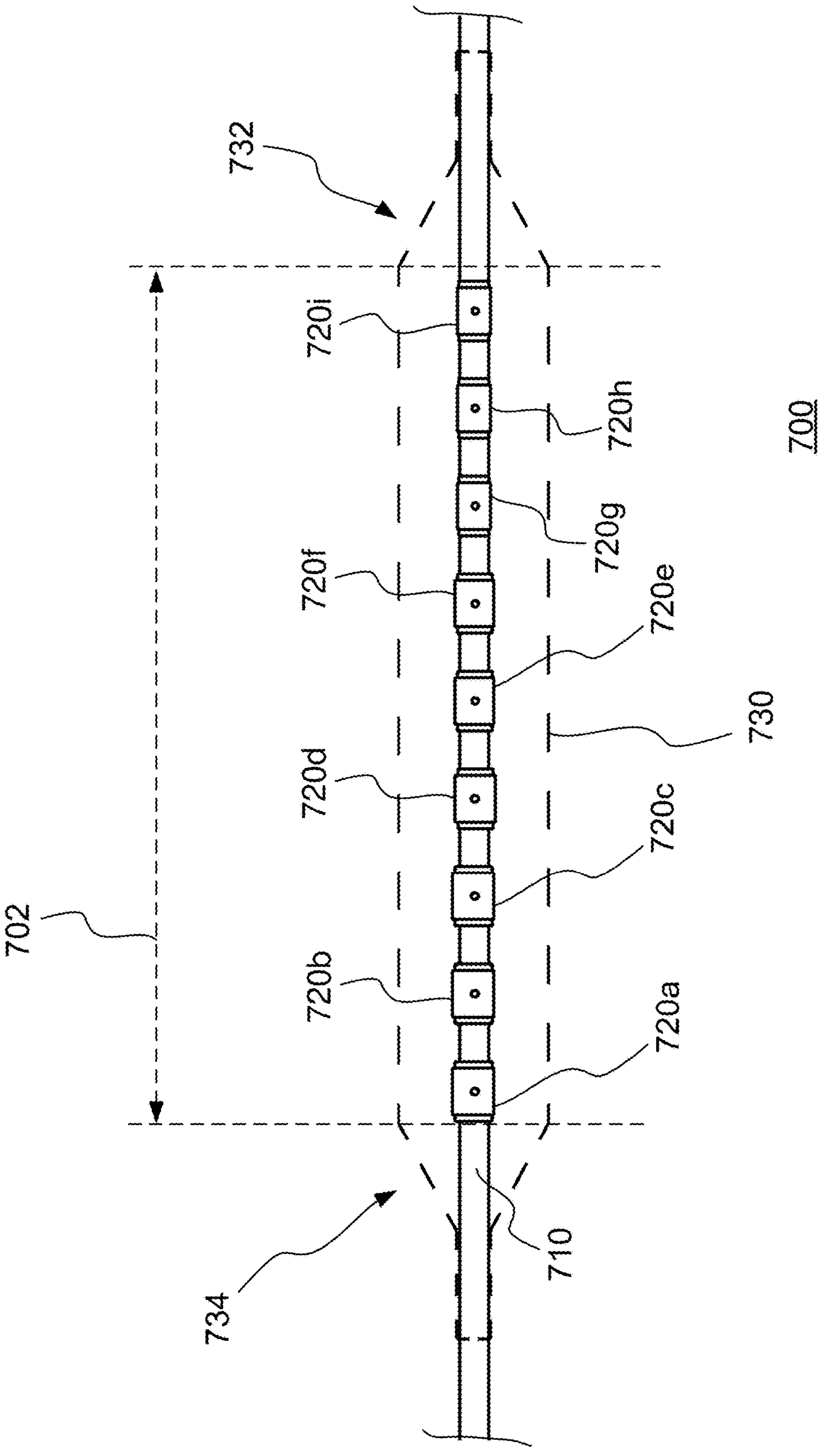
FIG. 7 illustrates a distal region of a catheter, according to some embodiments.

FIG. 7 illustrates a distal region of a catheter 700 that includes proximal shock wave emitters 720*a*-720*c*, central shock wave emitters 720*d*-720*f*, and distal shock wave emitters 720*g*-720*i*, according to aspects of the disclosure. Shock wave emitters 720*a*-720*i* may be enclosed within an enclosure 730 that is fillable with a conductive fluid. Shock wave emitters 720*a*-720*i* may be positioned along elongate member 710. In some embodiments, enclosure 720 is an angioplasty balloon having a semi-compliant balloon wall. In some embodiments, enclosure 720, in a deflated state, is pleated and folded during delivery through a body lumen (e.g., an artery or vein) and then filled and inflated to a pressure less than 5 atm at the treatment site.

In the deflated state, catheter 700 may have, along its working length 702: (i) a proximal outer diameter $OD_p$ on a proximal side 734 measured at a location of an emitter (e.g., emitter 720*a*, 720*b*, 720*c*) located on the proximal side 734 and (ii) a distal outer diameter $OD_d$ on a distal side 732 measured at a location of an emitter (e.g., emitter 720*g*, 720*h*, 720*i*) located on the distal side 732, where $OD_d < OD_p$. A smaller distal outer diameter $OD_d$ may improve delivery of catheter 700 through the body lumen to the treatment site.

In some embodiments, catheter 700, in the deflated state, includes a central outer diameter $OD_c$ measured at a location of an emitter (e.g., emitters 720*d*, 720*e*, 720*f*) located between proximally and distally positioned emitters, where $OD_d < OD_c < OD_p$.

In some embodiments, at least one of proximal emitters 720*a*, 720*b*, 720*c* has an outer diameter greater than at least one of distal emitters 720*g*, 720*h*, 720*i*. In some embodiments, at least one of central emitters 720*d*, 720*e*, 720*f* has an outer diameter greater than at least one of distal emitters 720*g*, 720*h*, 720*i*. In some embodiments, at least one of central emitters 720*d*, 720*e*, 720*f* has an outer diameter greater than at least one of distal emitters 720*g*, 720*h*, 720*i*. In some embodiments, at least one of central emitters 720*d*, 720*e*, 720*f* has an outer diameter less than at least one of proximal emitters 720*a*, 720*b*, 720*c*. In some embodiments, shock wave emitters 720*a*-720*i* have one of three different emitter outer diameters. Emitters having different outer diameters may include emitter bands having different sizes.

According to aspects of the disclosure, conductors, such as insulated wires, extend from a voltage pulse generator along the length of elongate member 710 to deliver voltage pulses to emitters 720*a*-720*i*. Emitters 720*a*-720*c* may be connected in series to a first channel of the voltage pulse generator, emitters 720*d*-720*f* may be connected in series to a second channel of the voltage pulse generator, and a emitters 720*g*-720*i* may be connected in series to a third channel of the voltage pulse generator. Because electrical connection to each channel requires separate wiring (via one or more conductors) to the emitters, the catheter may need to accommodate more conductors at the central and proximal regions of the enclosure 730. By including progressively larger emitter bands at the central and/or proximal regions, more conductors may be positioned under the emitter bands at those locations.

While the drawing figures illustrate catheters having two or three different emitters sizes, catheters in some embodiments may include four or more differently sized emitters to, for example, accommodate additional conductors. Further, in some embodiments, smaller diameter emitters may be positioned at the proximal region of the enclosure; such a configuration may help make the catheter easier to withdraw from a treatment site after shock wave therapy.

Figure 8:
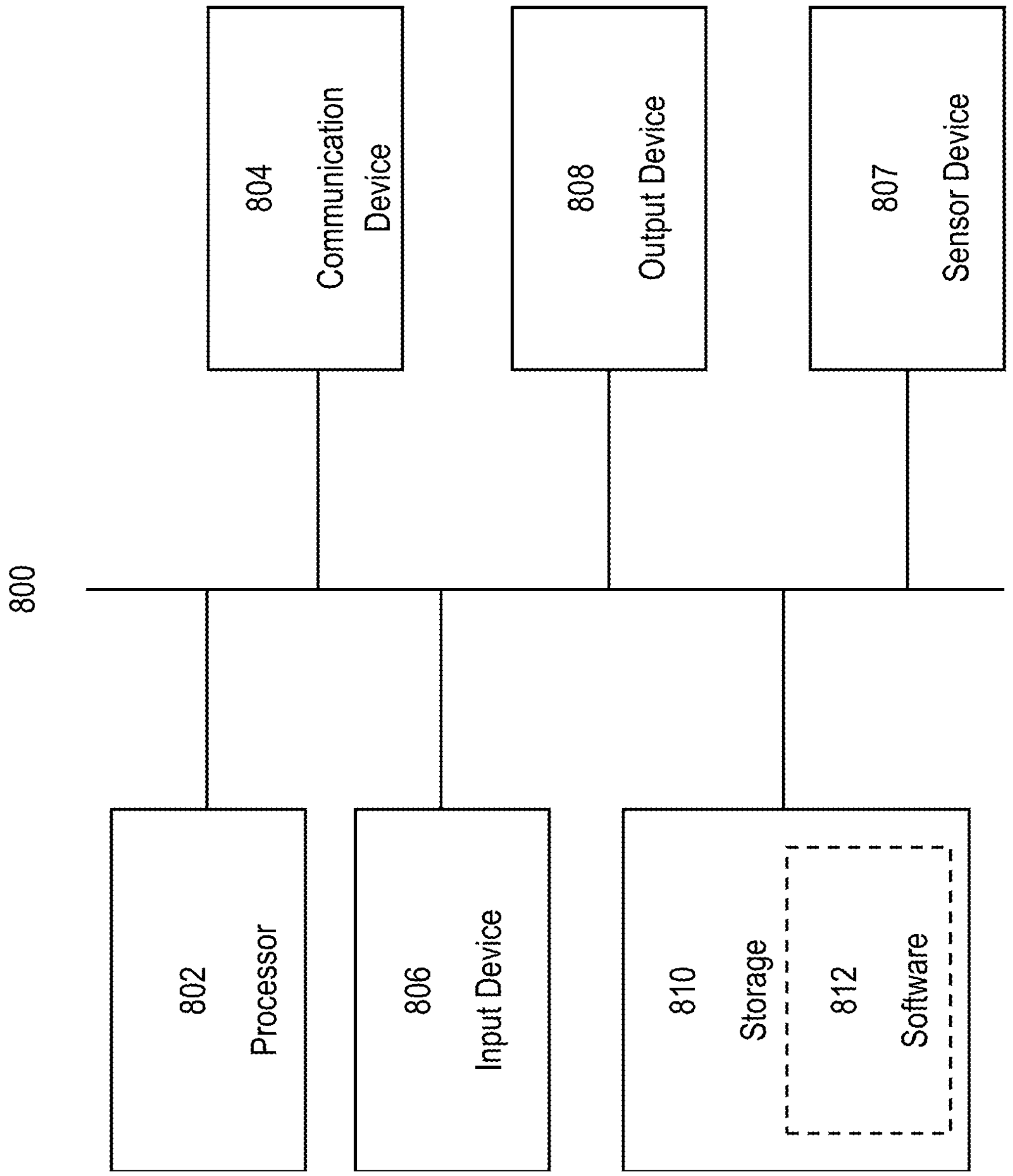
FIG. 8 illustrates a computing system, according to some embodiments.

FIG. 8 illustrates an example of a computing system 800 that may be used with one or more of the catheters and voltage pulse generators described herein. System 800 can be a computer connected to a network, such as one or more networks of hospital, including a local area network within a room of a medical facility and a network linking different portions of the medical facility, or a wide-area network accessed through the internet or other means. System 800 can be a client or a server. System 800 can be any suitable type of processor-based system, such as a personal computer, workstation, server, handheld computing device (portable electronic device), such as a phone or tablet, or dedicated device. System 800 can include, for example, one or more of input device 820, output device 830, one or more processors 810, storage 840, and communication device 860. Input device 820 and output device 830 can generally correspond to those described above and can either be connectable or integrated with the computer.

Input device 820 can be any suitable device that provides input, such as a touch screen, keyboard or keypad, mouse, gesture recognition component of a virtual/augmented reality system, or voice-recognition device. Output device 830 can be or include any suitable device that provides output, such as a display, touch screen, haptics device, virtual/augmented reality display, or speaker.

Storage 840 can be any suitable device that provides storage, such as an electrical, magnetic, or optical memory including a RAM, cache, hard drive, removable storage disk, or other non-transitory computer-readable medium. Communication device 860 can include any suitable device capable of transmitting and receiving signals over a network, such as a network interface chip or device. The components of the computing system 800 can be connected in any suitable manner, such as via a physical bus or wirelessly.

Processor(s) 810 can be any suitable processor or combination of processors, including any of, or any combination of, a central processing unit (CPU), field programmable gate array (FPGA), and application-specific integrated circuit (ASIC). Software 850, which can be stored in storage 840 and executed by one or more processors 810, can include, for example, the programming that embodies the functionality or portions of the functionality of the present disclosure (e.g., as embodied in the devices as described above), such as programming for performing one or more steps of any of the methods described herein.

Software 850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by or in connection with an instruction execution system, apparatus, or device. The transport computer-readable medium can include, but is not limited to, an electronic, magnetic, optical, electromagnetic, or infrared wired or wireless propagation medium.

System 800 may include a sensor device 870 that provides sensor data for processing by processor 810. Sensor device 870, in some embodiments, may be an imaging sensor that provides imaging data, for a lesion being treated. In some embodiments, sensor device 870 may be a voltage sensor, a current sensor, a pressure sensor, a temperature sensor, or an optical sensor for providing data about a state of the catheter or a lesion.

System 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

System 800 can implement any operating system suitable for operating on the network. Software 850 can be written in any suitable programming language, such as C, C++, Java, or Python. In various examples, application software embodying the functionality of the present disclosure can be deployed in different configurations, such as in a client/server arrangement or through a Web browser as a Web-based application or Web service.

System 800 may be configured to selectively control the delivery of energy from one or more of energy sources (e.g., a voltage pulse generator or a light energy source) to one or more acoustic energy emitters (e.g., a forward-firing emitter, a radially-firing emitter, an unenclosed emitter, or an enclosed emitter) depending on input from input device 820.

System 800 may be configured to tune the energy properties of energy delivered to one or more of the above-described emitters based on tissue properties received from sensor device 870. Tissue properties may include lesion tissue type (e.g., calcific, thrombic, fibrotic), lesion morphology (e.g., thickness, length, eccentricity).

It should be noted that the elements and features of the example catheters illustrated throughout this specification and drawings may be rearranged, recombined, and modified without departing from the present invention. For instance, while this specification and drawings describe and illustrate catheters having several example emitter assembly designs, the present disclosure is intended to include catheters having a variety of emitter assembly configurations. The number, placement, and spacing of the electrode pairs of the shock wave generators can be modified without departing from the subject invention. Further, the number, placement, and spacing of enclosures of catheters can be modified without departing from the subject invention.

Although the catheter devices described herein have been discussed primarily in the context of treating coronary occlusions, such as lesions in vasculature, the catheter devices described herein can be used for a variety of occlusions, such as occlusions in the peripheral vasculature (e.g., above-the-knee, below-the-knee, iliac, carotid, etc.). For further examples, various embodiments may be used for treating soft tissues, such as cancer and tumors (i.e., non-thermal ablation methods), blood clots, fibroids, cysts, organs, scar and fibrotic tissue removal, or other tissue destruction and removal treatments. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal, and destruction of tissue, or used in place of thermal treatments or cauterization for venous insufficiency and fallopian ligation (i.e., for permanent female contraception).

In one or more examples, the electrode assemblies and, catheters described herein could also be used for tissue engineering methods, for instance, for mechanical tissue decellularization to create a bioactive scaffold in which new cells (e.g., exogenous and endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It will be understood that the foregoing is only illustrative, and that various modifications, alterations and combinations can be made by those skilled in the art without departing from the scope and spirit of the disclosure. Any of the variations of the various catheters disclosed herein can include features described by any other catheters or combination of catheters herein. Furthermore, any of the methods can be used with any of the catheters disclosed. Accordingly, it is not intended that the systems, catheters, and methods described herein be limited, except as by the appended claims.

The invention claimed is:

1. A catheter for treating a lesion in a body lumen, the catheter comprising:

an elongate member extending from a proximal region of the catheter to a distal region of the catheter;

a distal shock wave emitter having a distal outer diameter and located at the distal region of the catheter, wherein the distal shock wave emitter is the distal most shock wave emitter;

a proximal shock wave emitter having a proximal outer diameter greater than the distal outer diameter and located proximally of the distal shock wave emitter, wherein the proximal shock wave emitter is the proximal most shock wave emitter, and an enclosure having:

a central region surrounding the distal shock wave emitter and the proximal shock wave emitter;

a proximal region proximal of the central region and having a proximal leg portion and a proximal tapering portion connecting the proximal region and the central region; and a distal region distal of the central region and having a distal leg portion and a distal tapering portion connecting the distal region and the central region.

2. The catheter of claim 1, wherein the difference between the distal outer diameter and the proximal outer diameter is at least 0.0254 mm.

3. The catheter of claim 1, wherein the difference between the distal outer diameter and proximal outer diameter is at least 0.0381 mm.

4. The catheter of claim 1, wherein the distal outer diameter is at most 98% of the proximal outer diameter.

5. The catheter of claim 1, wherein the distal outer diameter is at most 97.5% of the proximal outer diameter.

6. The catheter of claim 1, wherein a longitudinal distance from a center of the distal shock wave emitter to a center of the proximal shock wave emitter is no less than 6 mm.

7. The catheter of claim 6, wherein the longitudinal distance from the center of the distal shock wave emitter to the center of the proximal shock wave emitter is at least 7 mm.

8. The catheter of claim 1, wherein the distal shock wave emitter comprises a distal electrode pair and the proximal shock wave emitter comprises a proximal electrode pair.

9. The catheter of claim 8, wherein:

the distal electrode pair comprises a distal outer electrode and a distal inner electrode and the proximal electrode pair comprises a proximal outer electrode and a proximal inner electrode, and an outer diameter of the distal outer electrode is less than an outer diameter of the proximal outer electrode.

10. The catheter of claim 1, wherein the distal shock wave emitter and the proximal shock wave emitter are independently wired to a voltage pulse generator.

11. The catheter of claim 1, further comprising a distal conductor that extends from a voltage pulse generator to the distal shock wave emitter and a proximal conductor that extends from the voltage pulse generator to the proximal shock wave emitter and not the distal shock wave emitter.

12. The catheter of claim 1, further comprising an intermediate shock wave emitter having an intermediate outer diameter greater than the distal outer diameter and less than the proximal outer diameter and located proximally of the distal shock wave emitter.

13. The catheter of claim 1, wherein the catheter comprises four distal shock wave emitters and four proximal shock wave emitters.

14. The catheter of claim 1, wherein the catheter comprises two proximal shock wave emitters and a single distal shock wave emitter.

15. The catheter of claim 1, wherein, when the enclosure is filled with a fluid to a pressure between 0.5 atm and 5 atm, the central region tapers in diameter.

16. A shock wave catheter for treating a lesion in a body lumen with shock waves, the catheter comprising:
- an elongate member extending from a proximal region of the catheter to a distal region of the catheter;
- a plurality of shock wave emitters located at the distal region of the catheter; and
- an enclosure having:
  - a distal portion;
  - a proximal portion; and
  - a central portion located between the distal portion and the proximal portion and surrounding the plurality of shock wave emitters,
- wherein:
  - in a first configuration, the enclosure is substantially collapsed and a proximal outer diameter of the catheter at a proximal side of the central portion is greater than a distal outer diameter of the catheter at a distal side of the central portion, and,
  - in a second configuration, the enclosure is inflated with a fluid and the proximal outer diameter of the catheter is no less than the distal outer diameter.

17. The catheter of claim 16, wherein, in the first configuration, the difference between the distal outer diameter and the proximal outer diameter is at least 0.2 mm.

18. The catheter of claim 16, wherein, in the first configuration, the difference between the distal outer diameter and proximal outer diameter is at least 0.4 mm.

19. The catheter of claim 16, wherein, in the first configuration, the distal outer diameter is no greater than 98% of the proximal outer diameter.

20. The catheter of claim 16, wherein, in the first configuration, the distal outer diameter is no greater than 97.5% of the proximal outer diameter.

21. The catheter of claim 16, wherein the plurality of shock wave emitters comprises a proximal shock wave emitter and a distal shock wave emitter, wherein a longitudinal distance from a center of the distal shock wave emitter to a center of the proximal shock wave emitter is at least 6 mm.

22. The catheter of claim 21, wherein the longitudinal distance from the center of the distal shock wave emitter to the center of the proximal shock wave emitter is at least 7 mm.

23. The catheter of claim 22, wherein the distal shock wave emitter comprises a distal electrode pair and the proximal shock wave emitter comprises a proximal electrode pair.

24. The catheter of claim 23, wherein:
- the distal electrode pair comprises a distal outer electrode and a distal inner electrode and the proximal electrode pair comprises a proximal outer electrode and a proximal inner electrode, and
- an outer diameter of the distal outer electrode is less than an outer diameter of the proximal outer electrode.

25. The catheter of claim 22, wherein the distal shock wave emitter and the proximal shock wave emitter are independently wired to a power supply.

26. The catheter of claim 22, wherein the plurality of shock wave emitters comprises four distal shock wave emitters and four proximal shock wave emitters.

27. A shock wave catheter for treating a lesion a body lumen with shock waves, the catheter comprising:
- an elongate member extending form a proximal region of the catheter to a distal region of the catheter;
- a distal shock wave emitter comprising a distal inner band and a distal outer band having a distal outer diameter, wherein the distal shock wave emitter is the distal most shock wave emitter; and
- a proximal shock wave emitter comprising a proximal inner band and a proximal outer band having a proximal outer diameter greater than the distal outer diameter, wherein the proximal shock wave emitter is the proximal most shock wave emitter.

28. The shock wave catheter of claim 27, wherein the distal inner band is thinner than the proximal inner band.

29. The shock wave catheter of claim 27, wherein the distal inner band has the same thickness as the proximal inner band.

30. The shock wave catheter of claim 27, wherein the distal shock wave emitter includes a distal insulative layer, the proximal shock wave emitter includes a proximal insulative layer, and the distal insulative layer is thinner than the proximal insulative layer.

31. The shock wave catheter of claim 27, wherein the distal shock wave emitter includes a distal insulative layer, the proximal shock wave emitter includes a proximal insulative layer, and the distal insulative layer is the same thickness as the proximal insulative layer.

* * * * *